United States Patent [19]

Bley et al.

[11] Patent Number: 5,855,615
[45] Date of Patent: Jan. 5, 1999

[54] CONTROLLER EXPANSION SPHINCTER AUGMENTATION MEDIA

[75] Inventors: Robert Steven Bley, Menlo Park; Kevin H. Van Bladel, San Mateo, both of Calif.

[73] Assignee: Menlo Care, Inc., Menlo Park, Calif.

[21] Appl. No.: 660,127

[22] Filed: Jun. 7, 1996

[51] Int. Cl.⁶ .................................................. A61F 2/02
[52] U.S. Cl. ....................................................... 623/1
[58] Field of Search ........................................ 623/11, 12

[56] References Cited

U.S. PATENT DOCUMENTS

| | | | |
|---|---|---|---|
| Re. 32,969 | 6/1989 | Trager et al. | 424/81 |
| 3,419,006 | 12/1968 | King | 128/268 |
| 3,971,376 | 7/1976 | Wichterle | 128/260 |
| 4,134,871 | 1/1979 | Otani et al. | 260/29.6 |
| 4,197,846 | 4/1980 | Bucalo | 128/218 |
| 4,272,518 | 6/1981 | Moro et al. | 424/81 |
| 4,404,183 | 9/1983 | Kawata et al. | 424/19 |
| 4,423,099 | 12/1983 | Mueller et al. | 428/35 |
| 4,527,293 | 7/1985 | Eckstein et al. | 623/12 |
| 4,698,373 | 10/1987 | Tateosian et al. | 522/95 |
| 4,773,393 | 9/1988 | Haber et al. | 600/30 |
| 4,777,200 | 10/1988 | Dymond et al. | 524/458 |
| 4,803,075 | 2/1989 | Wallace et al. | 424/423 |
| 4,828,828 | 5/1989 | Trager et al. | 424/81 |
| 5,007,940 | 4/1991 | Berg | 623/66 |
| 5,067,965 | 11/1991 | Ersek et al. | 623/66 |
| 5,162,430 | 11/1992 | Rhee et al. | 525/54.1 |
| 5,330,768 | 7/1994 | Park et al. | 424/501 |
| 5,336,263 | 8/1994 | Ersek et al. | 623/11 |
| 5,514,754 | 5/1996 | Henderson et al. | 525/296 |
| 5,516,532 | 5/1996 | Atala et al. | 623/11 |
| 5,667,778 | 9/1997 | Atala | 623/11 |

FOREIGN PATENT DOCUMENTS

| | | |
|---|---|---|
| A-0 251 695 | 6/1987 | European Pat. Off. . |
| WO-A-86 01813 | 3/1986 | WIPO . |
| WO-A-93 16658 | 9/1993 | WIPO . |
| WO-A-93 19702 | 10/1993 | WIPO . |

OTHER PUBLICATIONS

Aesthetic Plastic Surgery, vol. 16, No. 1, 1992 NY, USA, pp. 59–65, Author R.A. Ersek et al, Title [Bioplastique : A New Biphasic Polymer for Minimally Invasive Injection Implantation].

Primary Examiner—David Isabella
Assistant Examiner—John M. Black
Attorney, Agent, or Firm—Hal Brent Woodrow

[57] ABSTRACT

A composition for injecting into tissues surrounding the urethra or ureter. It comprises a plurality of physiologically acceptable solid polymer particles dispersed in a physiologically acceptable biodissipatable liquid carrier. The polymer comprises a hydrophilic component. The solid polymer particles are a glycerine insoluble poly(ethylene oxide) (PEO) polymer or copolymer or a mineral oil insoluble polyvinylpyrrolidone polymer or copolymer. The plurality of solid polymer particles are capable of hydrating and upon hydration of absorbing at least about 30% water and of swelling to a predetermined volume. The solid particles are substantially insoluble in body fluids and substantially insoluble in and non-swellable by the liquid carrier. The composition is especially suitable in treating patients with urinary incontinence and patients with vesicoureteral reflux via injection into the tissues around the urethra or ureter.

37 Claims, 2 Drawing Sheets

CONTROLLER EXPANSION SPHINCTER AUGMENTATION MEDIA

TECHNICAL FIELD

The invention relates to a composition comprising solid polymer particles dispersed in a biodissipatable, generally nonaqueous, carrier liquid. The invention further relates to a method of deforming a selected tissue structure by inserting into tissues adjacent to the selected tissue structure such a composition. More specifically, the invention provides a treatment for those with urinary incontinence and/or vesicoureteral reflux.

BACKGROUND OF THE INVENTION

Surgical implantation of artificial sphincters has often been employed to treat patients suffering from urinary incontinence. The surgical implantation of the artificial sphincter commonly requires hospitalization. In addition, such a procedure is relatively complex and expensive, and will usually require six to eight weeks of recovery time. Moreover, often time, the procedure is unsuccessful or the artificial sphincter malfunctions. As a result, additional surgery is required to adjust, repair or replace the implant.

In the recent past, urinary incontinence may be successfully treated by using nonsurgical means. A common and widely used method to treat patients with urinary incontinence is periurethral injection of a composition commercially sold in Canada as "Polytef" and as "Urethrin". "Polytef" is a paste comprising a fifty-fifty (50/50) by weight (corresponding to about 64:36 by volume) mixture of glycerine liquid and Teflon particles. However, after injection, over a period of time the glycerine is readily dissipated into the body and then metabolized or eliminated, leaving only the Teflon particles. This means that only fifty (50) percent of the injected weight remains at the injection site. Consequently the surgeon must inject significantly more volume than he thinks he will need and at times must actually close down the urethra further than is desired. This closure could possibly be complete and thus put the patient into temporary urinary retention. Additionally, the fact that a large portion of the volume disappears makes it difficult for the surgeon to visually gauge how much is an appropriate amount of the Teflon paste to inject. As a result, the surgeon is likely to not inject enough paste volume. The procedure therefore may fail, and a second or even a third procedure to inject additional paste may be required. An additional drawback of the Teflon paste is that the Teflon particle size is sufficiently small so as to allow the particles to migrate to other locations of the body such as the lungs, brain, etc. Teflon particles have been known to induce tissue reaction and form Teflon-induced granulomas in certain individuals. This tissue reaction to Teflon has caused concerns for the patient's safety. Also, the Teflon paste is highly viscous and can only be injected using a hypodermic held by an injection assist device since the surgeon would not have sufficient strength to force the highly viscous Teflon paste through a needle of any acceptable size.

An alternative to using the Teflon paste is using a collagen suspension. The collagen suspension is injected in the same manner as Teflon paste so as to form a fibrous mass of tissue around the augmentation site. This fibrous mass created by the collagen injection, however, decreases in size and breaks down over time as it is eventually eliminated by the patient's body. As a result, additional injections are periodically required.

Another alternative is to inject silicone particles dispersed in an aqueous, polyvinylpyrrolidone solution. This combination has the same problems as the Teflon paste in that the polyvinylpyrrolidone solution is readily dissipated away from the area of injection leaving only the volume of silicone particles remaining and in that due to its high viscosity a great deal of force is necessary to inject the silicone dispersion through a needle of an acceptable size whereby it is necessary for the surgeon to utilize an injection assist device to accomplish injection.

Another material that has been injected is autologous fat. This has had similar problems as the collagen in that the body eventually breaks it down and it disappears.

Devices have been made to attempt to overcome these problems. One device is an inflatable silicone sphere that is passed through a needle and is inflated with saline in the same area that the other materials are injected. There are, however, some problems associated with this device. It is a delicate, mechanical device that is capable of mechanical failure of the valves, shells and structural joints.

Accordingly, it would be desirable to have a composition wherein the mixture has sufficiently low viscosity so that it is not necessary to utilize an injection assist device to inject it whereby it is easily administered via injection, generally will not swell or contract to an undesired extent, will be soft enough so as to not cause tissue response/reaction while still being firm enough to provide the required constriction, will not dissipate and will not migrate from the site of injection, thereby enabling the urethra to maintain the initial surgical constriction.

DISCLOSURE OF THE INVENTION

The present invention is directed to overcoming one or more of the problems as set forth above.

One embodiment of the invention is a physiologically acceptable composition comprising a plurality of physiologically acceptable polymer particles dispersed in a physiologically acceptable biodissipatable liquid carrier. The polymer particles are a poly(ethylene oxide) (PEO) polymer or copolymer or a polyvinylpyrrolidone polymer or copolymer which is capable of hydrating, and upon hydration swelling to a predetermined volume. In accordance with a preferred form of this embodiment the liquid carrier is substantially non-aqueous and the solid polymer particles are substantially insoluble in the liquid carrier and in body fluids.

Another embodiment of the invention is a method of deforming a selected tissue structure by inserting into the tissues adjacent to the tissue structure the above-described physiologically acceptable composition.

Still another embodiment of the invention is a method for increasing urine flow resistance in a patient having urinary incontinence by inserting into the tissues surrounding the patient's urethra, adjacent to the patient's urethral sphincter, the above-described physiologically acceptable composition.

Yet another embodiment of the invention is a method for ureteral augmentation in a patient having vesicoureteral reflux by inserting into the tissues adjacent to the patient's ureteral orifice the above-described physiologically acceptable composition.

Accordingly, the invention provides a nonsurgical, procedure using an easily administered low viscosity composition for treating patients with urinary incontinence. In addition, the invention can reduce the need for re-injections associated with the use of Teflon, collagen, silicone, autologous fat or other similar materials when treating patients with urinary incontinence. By having physiologically acceptable solid polymer particles that will not break down, will not migrate (due to their increased size after swelling), will not lead to adverse tissue reaction and can be injected without use of an injection assist device due to the low viscosity of the solution form which they are introduced, a more permanent repair is given to the incontinent patient. Similarly, because of the composition's properties, it can be used to treat patients suffering from vesicoureteral reflux.

BRIEF DESCRIPTION OF THE DRAWINGS

The invention will be better understood by reference to the figures of the drawings wherein like numbers denote like parts throughout and wherein.

BEST MODE FOR CARRYING OUT THE INVENTION

The physiologically acceptable composition can be used in various medical situations. Typically, the physiologically acceptable composition can be injected into tissues adjacent to a selected tissue structure thereby deforming the selected tissue structure. Preferred uses for this particular application are: 1) to provide a treatment for those with urinary incontinence wherein the urethra cannot be properly constricted to prevent passage of urine from the bladder, and 2) to provide a treatment for those with vesicoureteral reflux wherein the ureter cannot properly constrict to prevent backflow of urine from the bladder up the ureter.

Figure 1:
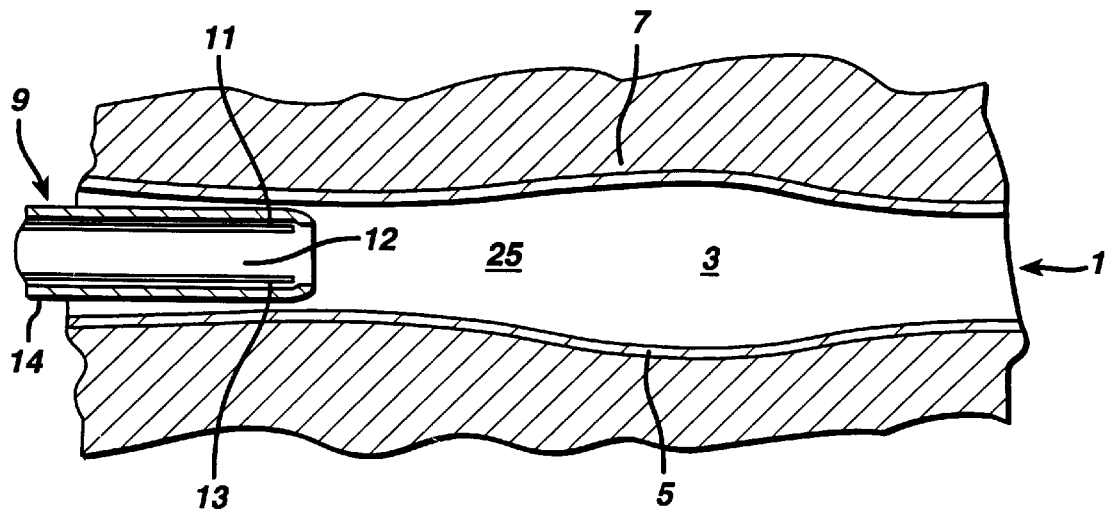
FIG. 1 is a longitudinal section of a tissue structure, more specifically a urethra/ureter, with an enlarged lumen surrounded by muscle tissues.

Referring to FIG. 1, there is shown a urethra/ureter 1 having a wall 5 and an enlarged lumen 3. The urethra/ureter 1 is surrounded by tissues 7. Before the enlarged lumen 3 is to be constricted with the physiologically acceptable composition, a cystoscope 9 comprising a fiberoptic light transmitting element 11, a working channel 12 and a viewing element 13 encased in a metallic sheath 14 is inserted up the urethra/ureter to a distance close to the enlarged lumen 3. The close distance is selected to allow a clear view of the enlarged lumen 3.

Figure 2:
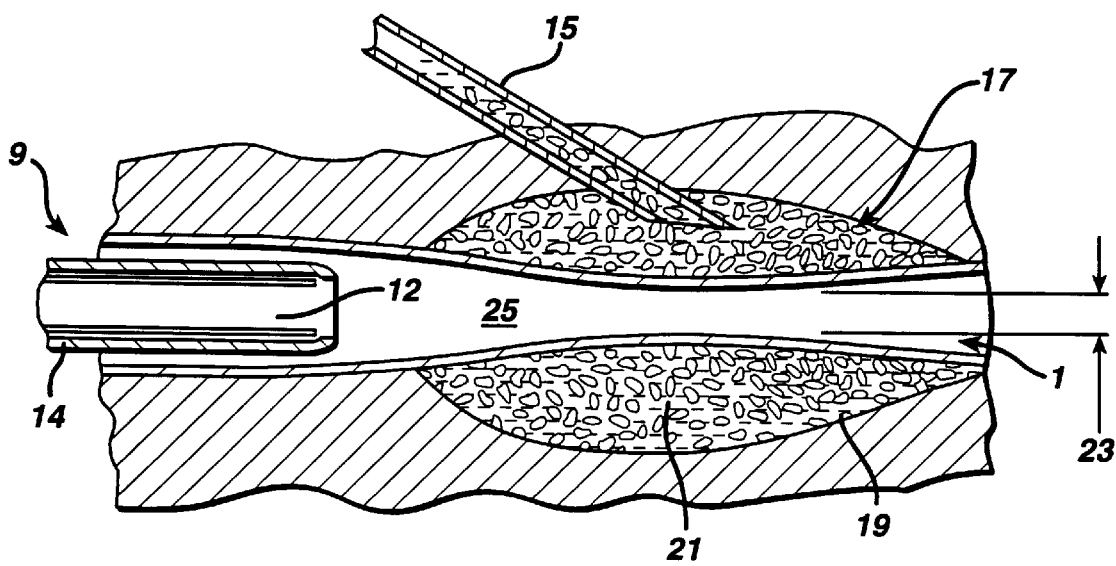
FIG. 2 shows the same longitudinal section immediately after a physiologically acceptable composition has been injected around the enlarged lumen of the urethra using an externally inserted needle technique.

Once the enlarged lumen 3 is readily in view, referring more specifically to FIG. 2, a hypodermic needle 15 is inserted through the tissues 7, preferably over the enlarged lumen 3, stopping near the wall 5 of the enlarged lumen 3. Thereafter, a physiologically acceptable composition 17 is injected via the hypodermic needle 15 into the tissues 7 adjacent the wall 5.

Figure 4:
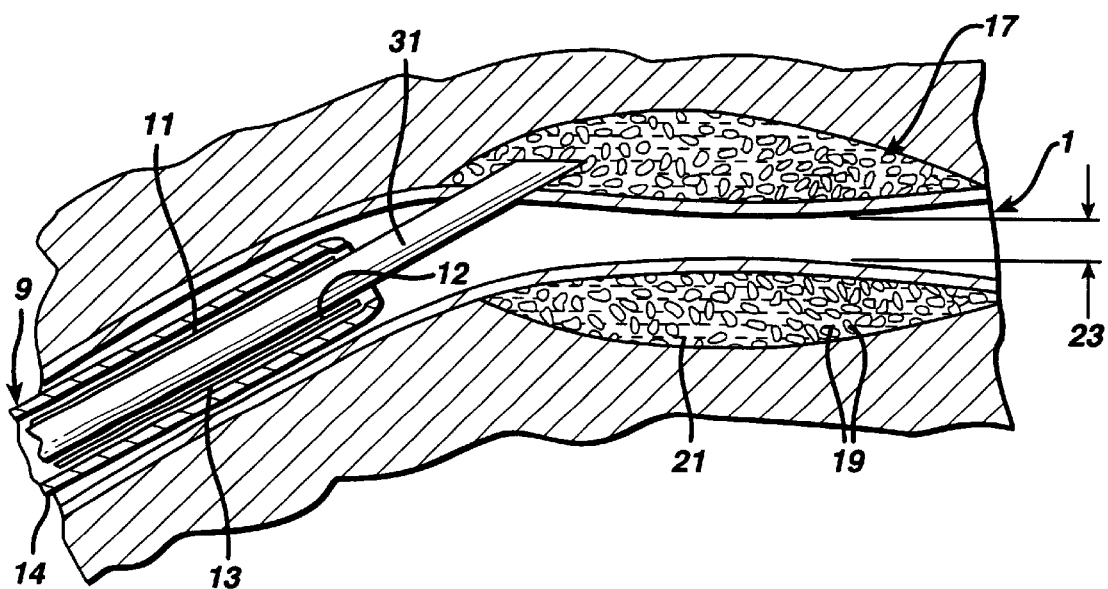
FIG. 4 shows the same longitudinal section as in FIG. 1 immediately after a physiologically acceptable composition has been injected around the enlarged lumen of the urethra/ureter utilizing a through the cystoscope injection technique.

As an alternative, and as is illustrated in FIG. 4, an elongated needle 31 may be inserted through the working channel 12, into the urethra/ureter 1 and the surrounding tissue and the injection can be completed operating solely through the cystoscope 9. This is generally the preferred method of operation, on male patients and is the preferred method for male and female patients for the ureter.

The physiologically acceptable composition 17 comprises a plurality of solid polymer particles 19 dispersed in a physiologically acceptable biodissipatable liquid carrier 21 in which they preferably do not swell for at least the time it takes to insert them in a patient. Preferably the particles do not swell for at least a month of storage, more preferably at least a month and still more preferably at least several, for example, 3 or more, months. The term "solid" is used broadly to indicate the phase of the particles. Such particles may contain one or more hollow spaces within their volumes. The carrier 21 may contain a considerable quantity of water dissolved therein so long as the water does not swell the solid polymer particles 19 when they are suspended in the carrier 21. Indeed, when the preferred polymer, PEO, is used in its preferred liquid carrier, glycerine, it is advantageous to have a considerable quantity of water or other viscosity reducing agent in the glycerin to provide a lowered viscosity suspension for ease of injection.

The solid polymer particles 19 suitable for the present invention must be physiologically acceptable and are preferably substantially insoluble in the liquid carrier 21 and in body fluids. The solid polymer 19, in a selected concentration, must be able to hydrate and swell to a predetermined volume as the liquid carrier 21 dissipates, the predetermined volume generally being substantially equal to the initial volume of the composition 17.

The solid unhydrated polymer 19 comprises a hydrophilic component and should have a particle size, when unhydrated, which is small enough to allow the formation of a paste which is readily injectable via a needle. On hydration occurring following injection the particles preferably have a particle size sufficient to avoid migration. Migration to other parts of the body should be prevented because the particle may cause tissue reaction. One way of obtaining solid unhydrated polymer particles 19 of the desired size is by cryogenic grinding of a larger piece or pieces of polymer.

The hydrophilic component is suitably a poly(ethylene oxide) polymer or copolymer or a polyvinylpyrrolidone polymer or copolymer that absorbs at least about 30% water, preferably at least about 50% water, more preferably about 100% water or more, e.g., 150% water, by weight based on the weight of the hydrophilic polymer. The hydrophilic polymer preferably forms a hydrogel on absorption of water. The hydrophilic polymer should not be degraded by body fluids within the site of injection for long periods of time, for example, one year, more preferably two years, still more preferably five years. Most preferably the hydrophilic polymer should be substantially completely non-degradable in that it should preferably be non-degradable for the life of the patient.

The degree of swelling of the polymer can be controlled or tailored as desired by controlling the amount of crosslinking of the polymer. The amount of crosslinking can be adjusted, as is well known in the art, chemically and/or by adjusting the amount of radiation applied to cause the crosslinking. The higher the degree of crosslinking, the less will be the swellability of the hydrated polymer. Generally, it is preferred that a relatively large swelling ratio be selected as this allows the use of relatively smaller particles whereby the viscosity of the injectate is lowered making for easier injection by the physician.

Any of a great variety of crosslinking agents known to the art may be utilized to accomplish the crosslinking. As non-limiting examples (other crosslinking agents may alternatively be used, as well), some preferred crosslinking agents are tetraethylene glycol diacrylate, tetraethylene glycol dimethacrylate, methylene bis-acrylamide, ethylene glycol dimethacrylate, high and low molecular weight polyethylene diacrylates and methacrylates, triallyl triazine trione, divinyl sulfone, diallytantradianide and pentaerythritol dimethacrylate.

If the composition 17 is fifty unit volume liquid carrier 21 and fifty unit volume solid polymer 19, it will generally be desirable to have the solid polymer 19 swell sufficiently upon hydration to compensate for the fifty unit volume lost by dissipation of the liquid carrier 21. For selected surgeries, it may be desirable to have the expansion volume of the solid polymer 19 exceed or fall short of the initial volume of the injected composition 17. Suitably the expansion percentage (of an particle) can be between about 300% and 3,000%, more usually between about 600% and 1500%. This would correspond to a bulk expansion of a plurality of particles (because of the interstitial space) of from about 50% to about 500%, more preferably from about 150% to about 350%.

Preferably, the solid polymer 19 is PEO (including copolymers thereof with, for example, polypropylene oxide, PPO). PEO having an initial (prior to irradiation and cross-linking) molecular weight of from 200,000 to 7,000,000 have been successfully tested in accordance with the invention and cross-linked using electron beam radiation and a cross-linking agent). The most preferred composition uses PEO having an initial molecular weight of about 400,000, a crosslinking agent as set forth above and applying from 5 to 15 Mrad of electron beam radiation.

The liquid carrier 21 of the present invention for the above-physiologically acceptable composition 17 is preferably one in which the solid polymer 19 preferably does not swell. For example, the liquid carrier 21 may be a nonaqueous, physiologically acceptable, biodissipatable liquid carrier. Also, as pointed out previously, the carrier 21 may contain a considerable quantity of water or other viscosity reducing agent dissolved therein so long as the water or other viscosity reducing agent does not significantly swell the solid polymer particles 19 when they are suspended in the carrier 21.

An aqueous liquid carrier can be used but only if it is mixed with the solid polymer particles a sufficiently short time before injection so that the solid polymer particles do not swell significantly prior to and during injection and/or if it hydrates over a sufficiently long period of time so as to allow it to be fully injected before significant, for example, 20% of its ultimate, swelling takes place. If desired, the solid polymer particles can be coated with a physiologically acceptable coating to delay hydration. This is particularly useful when an aqueous liquid serves as the carrier liquid.

The term biodissipatable as used herein is defined to mean that the liquid carrier (and the viscosity reducing agent) will not remain as such at the location injected but will instead exit that location by any method including, but not limited to, dissolving in body liquids and being carried away, being eliminated, being metabolized, being stored elsewhere, being absorbed by body tissue or by the solid polymer particles in the instance wherein the liquid carrier is aqueous or part aqueous or being volatilized. The biodissipatable liquid carrier 21 further should not act so as to significantly swell the solid polymer particles 19. This property will allow for long term storage of the composition 17. Examples of such biodissipatable liquid carriers are glycerin, glycerin with up to about 18% water dissolved in it, glycerol monoacetate, glycerol diacetate, polyethylene glycol, diethylene glycol, polyethylene glycol/polypropylene glycol block copolymers, low molecular weight polyethylene oxides, Polysorbate and mixtures of the above.

The biodissipatable liquid carrier may suitably have a biodissipatable viscosity reducing agent dissolved in it. The viscosity reducing agent, when the liquid carrier is glycerin, may suitably be water, isopropyl alcohol, alcohols of the formula $-CH_3-(CH_2)_x-OH$ where $x<4$, dialcohols of the formula $HO-(CH_2)_x-OH$ where $x,8$ or ethylene glycols with molecular weight less than 400. When the liquid carrier is a mineral oil suitable biodissipatable viscosity reducing agents are triglyceride oils such as cottonseed oil, corn oil, soybean oil and the like, hexane and heptane. The triglyceride oils are also suitable for and can serve as the liquid carrier.

The solid polymer 19 is mixed with the biodissipatable liquid carrier 21 in a selected concentration such that the solid polymer 19, upon hydrating in the body when in contact with body fluids, swells to a predetermined volume as the biodissipatable liquid carrier 21 dissipates. The predetermined volume is generally substantially equal to the initial volume of the injected composition. However, if desired, the predetermined volume can be selected to be more or less than the initial volume. It should be noted that the predetermined volume may not be precisely equal to the volume which results within a patient's body when the solid polymer 19 expands since other processes, for example fibrosis, may occur within the body which will lead to a different, usually somewhat larger volume, than would be expected from simply hydrating the solid polymer 19 in vitro. In such a case the size of the predetermined volume can be appropriately adjusted so that the total volume present in the patient's body at the injection site, following hydration, is as desired for the end therapeutic purpose.

In accordance with a preferred embodiment of the invention the amount of the solid polymer particles in the liquid carrier is made relatively low and the swelling ratio of the solid polymer particles is selected to be sufficiently high so that a relatively low viscosity suspension results. A viscosity reducing agent can be added to provide the desired low viscosity suspension for injection. This allows injection using a relatively small needle on a hypodermic syringe which has a piston which is operated by a force generated by the medical practitioners hand, rather than requiring use of a high pressure discharge providing dispensing gun, much like a caulking gun, as is necessary with prior art compositions. A typical composition might comprise no more than about 20%, by weight, of solid polymer particles, no more than about 20% by weight, of viscosity reducing agent and the remainder liquid carrier. In a sense, the viscosity reducing agent could be considered a part of an overall liquid carrier composition since the viscosity reducing agent is dissolved in the liquid carrier. They are distinguished in this discussion because of their different use in the overall injectable composition.

The viscosity of glycerin drops considerably (using a falling ball viscometer) as water content increases. Table 1 documents experiments carried out to measure the magnitude of the drop:

TABLE 1

| % water in glycerin | Viscosity |
| --- | --- |
| 0% | 629 centipoise |
| 3% | 376 cps |
| 5% | 272 cps |
| 7% | 234 cps |
| 12% | 103 cps |

The viscosity of the (pure) mineral oil utilized with the PVP formulation was also measured and was found to be 136 cps.

In no instance above was a suspension of polymer particles present. It is desirable that the viscosity of the carrier liquid not exceed about 1,000 cps, preferably not exceed 650 cps and more preferably not exceed 400 cps when measured as described so as to allow easy injection without use of an injection assist device.

Up to about 18% water can be added to glycerine without the water content being high enough so that significant swelling occurs of the PEO particles. Thus, 0 to 18% water can be added to the glycerine. The viscosity can, hence, be reduced even further than shown in the above table in this manner. However, as the viscosity drops the likelihood of the injected oozing from the injection wound becomes greater, whereby it is generally preferred to use an amount of water which falls in the range from about 5% to about 10%, more preferably from about 6% to about 9%, in the glycerine carrier. As indicated, glycerine can be used without any added water. Although the force required to inject the composition is greater, it is still quite possible for the medical practitioner to hand motivate a conventional hypodermic syringe to deliver the injected.

As the composition 17 is injected into the tissues 7 adjacent the wall 5 of the enlarged lumen 3, the diameter of the enlarged lumen 3 is observed through the cystoscope 9 for constriction. The composition 17 constricts the wall 5, decreasing the diameter of the once enlarged lumen 3 into a constricted area 23. With increasing volume of the composition 17, the constricted area 23 is further decreased. Once the desired degree of constriction is attained at the constricted area 23, injection of the composition 17 is stopped and the hypodermic needle 15 (or 31) is removed from the site of insertion. The constricted area 23, as observed through the cystoscope 9, would generally have an equal or smaller diameter than the diameter 25 of the rest of the urethra 1. When injections are made about the ureter and when injections are made in males the needle 15 is passed through the working channel 12 of the cystoscope 9 and through the wall of the urethra/ureter rather than through adjacent tissue as illustrated in FIG. 4.

Figure 3:
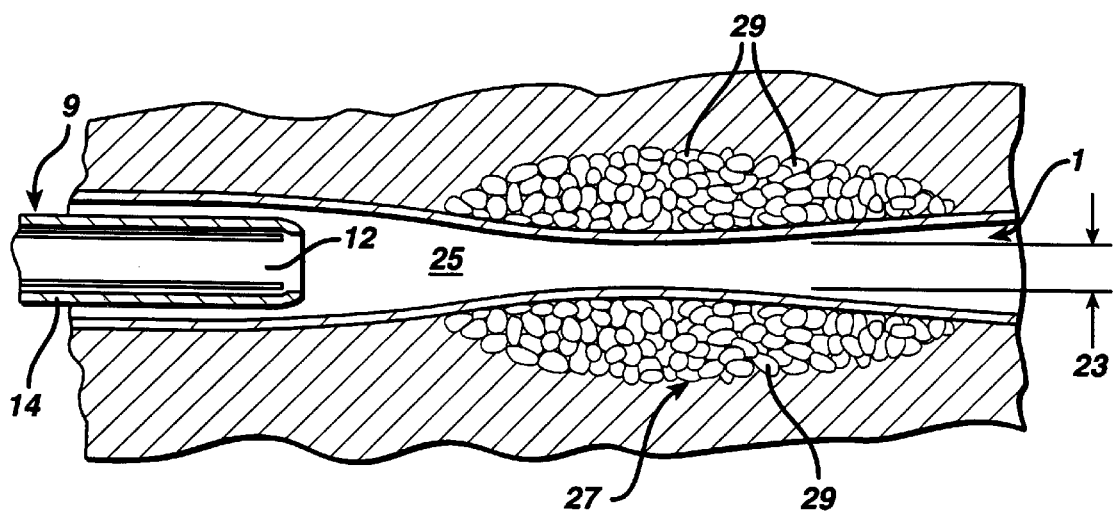
FIG. 3 shows the physiologically acceptable composition wherein the solid polymer particles have hydrated, swelled and agglomerated as the liquid carrier has dissipated.

Referring to FIG. 3, there is shown a solid structure 27 comprising hydrated and swelled solid polymer particles 29. The solid polymer particles 19 in FIG. 2, after the dissipation of the biodissipatable liquid carrier 21, hydrate and swell to the swelled solid polymer 29 (which may be in the nature of gels) having a volume which is substantially equal to the sum of the volumes of the dissipated liquid carrier 21 plus the volume of the unswelled solid polymer 19. As a result, the initial volume of the physiologically acceptable composition 17 is maintained. With the initial volume maintained, the constricted area 23 retains the desired degree of constriction. The ability of the solid polymer 19 to hydrate and swell, thereby maintaining the initial volume of the composition 17, therefore eliminates the need for repeated injections to maintain the desired degree of constriction. In addition, since the unswelled solid polymer 19 and the swelled solid polymer 29 are able to remain in place due to their particle size and insolubility in body fluids, the degree of constriction is substantially permanent. Further, the fact that the solid polymer particles 19 swell can lead to their attaining a size such that they resist or prevent migration from the site of injection. The literature is unclear in this area but appears to indicate that particles of 25 microns, 50 microns or 80 microns in size will resist migration. It should be noted that swelling in length (diameter in spherical particles) is proportional to the cube root of swelling in volume. Thus, very large swelling ratios may be desirable in certain instances so as to allow the composition to be prepared in readily injectable paste form while still providing swelled polymer particles of a size which will resist migration from the injection site.

In certain situations it can be desirable to add a radiopaque material to the solid polymer particles, preferably barium sulfate, bismuth subcarbonate, tantalum, tungsten, silver or mixtures thereof. The radiopaque material can be incorporated into the solid polymer from which the solid polymer particles are formed by melt mixing or, in the case of gels by dispersing into the solutions prior to crosslinking them to form gels. By having the solid polymer particles radiopaque, the constricted site 23, normally radiolucent to X-rays as with many other body tissues, will no longer be radiolucent. Consequently, the constricted area 23 can be examined by X-ray imaging or fluoroscopy which may help to visualize the internal shape within the tissue since this cannot be seen by direct observation through the cystoscope 9.

The invention will be better understood by reference to the following experimental examples:

EXAMPLE 1
Constant Volume Expansion Tests

This test verifies that the suspension can maintain constant volume after the carrier dissipates and the hydrogel particles hydrate.

2.5 cc of a suspension designed to maintain constant volume (a "constant volume" suspension) was injected into a 15 cc centrifuge tube filled with isotonic saline (similar to body fluids).

(Formulation: 10 ml suspension was prepared of 0.7022 gm (0.63 cc) crosslinked PEO in 11.641 gm of 11% water in glycerine solution).

The sample was mixed thoroughly. The glycerin dissipated into the saline and the crosslinked PEO particles swelled becoming gel particles. The sample was then centrifuged to determine the hydrated volume of the gel particles. The hydrated volume of the gel particles after centrifuging was 2.45 cc, within 2% of the initial injection volume of 2.5 cc.

This same formulation was sterilized using electron beam radiation of 2.5 Mrad. 2.0 cc sterilized suspension was injected into a 15 cc centrifuge tube filled with isotonic saline. After mixing and centrifuging, the hydrated volume was recorded as 2.0 cc. The hydrated volume was therefore the same as the initial injected volume.

This test was repeated many times on a variety of formulations to demonstrate that the expansion of the particles compensates for the lost carrier volume.

EXAMPLE 2
Injection Force Tests

As all bulking agent formulations (the term bulking agent refers to the injectate) are designed for endoscopic injection, a standardized test was designed to test the ultimate force required to move the bulking agent through specific needles. Use of this test permitted objective decision-making in process and formulation changes and the evaluation of delivery systems. A LLoyd, or Instron with a series of load cells rated between 5 and 500N was the equipment used.

The load cell was rezeroed between tests. The deformation of the rubber seal within the syringe plunger prevents complete unloading of the system via extrusion of bulking agent, and a residual load remains against the sensor. Backing off the crossarm and resetting the system results in a more accurate reading of the injection force.

When testing the bulking agent, the force curve generated by the instrument was observed. The test was continued long enough for the force reading to stabilize, and the curve to reach the asymptotic ultimate force. The general setting for the extension limit of the cross-arm was 0.5 inches, given the example below.

The purpose was to provide objective data on force required in injecting bulking formulas through syringe system. The material used was a bulking agent specimen. The equipment used was a Lloyd Material Testing System, syringe, needle, syringe fixtures, collection vial, and safety glasses. The Lloyd apparatus was a Chatillon Instron compression/tensile tester.

The injection forces of the constant volume suspensions with a range of water concentrations from 0% to 12% water were measured using the specified procedure. The suspensions were filled into 3 cc syringes. The syringes were connected to 4" 19 gauge needles. The syringe with needle was placed into a fixture where the force required to inject the material could be measured in a compression mode. The rate of injecting the suspensions were measured between 1 in/min to 5.5 in/min.

| Constant Volume Suspension | Injection Force @5.5 in/min |
| --- | --- |
| 0% water | 27.83 lb |
| 3% water | 13.47 lb |
| 5% water | 11.19 lb |
| 8% water | 7.09 lb |
| 12% water | 4.08 lb |

Teflon particles in glycerin and silicone particles in a PVP solution injection forces were both measured to be above 40 lb and caused the syringe to fail.

The syringe force testing showed that the forces for the constant volume suspensions were significantly lower than Teflon particles in glycerin or silicone particles in PVP solution. From this data it follows that, for use without an assist device the force should be limited to less than about 40 lb and it is preferred that the injection force be limited to less than or equal to about 30 lb so as to allow use of a conventional non-assist type syringe. More preferably, the injection force can be limited to less than or equal to about 20 lb.

EXAMPLE 3
Guinea Pig Subcutaneous Implantation

A constant volume suspension was injected into a guinea pig subcutaneously. The injection site width and length was measured and recorded with calipers. The dimensions of the injection site was monitored over a 3 month period. The injection site maintained increased dimensions during the entire 3 months; therefore, the injection material did not reduce in size during the 3 month time period.

EXAMPLE 4
Extravasation Tests

Three different constant volume suspensions with 3%, 6%, & 9% water were injected into the urethra wall of beagle dogs. The test was to determine the amount of water necessary to optimize the viscosity for easy injectability and minimal leakage or extravasation from the tissue after injection. It was determine that the range of 3%–9% is acceptable with respect to minimal extravasation and that suspensions with greater than 6% water had acceptable injection forces when using a hand driven syringe.

EXAMPLE 5
Beagle Dog Urethral Wall Implantation

The constant volume suspensions was injected in the area of final use in beagle dogs. The formulation was injected into the dogs urethra wall using a 20 gauge XXTW hypodermic tubing through a urinary scope. The dogs urethra were observed using a scope at 3, 7, 10, 14, 28 days. The boluses appeared to remain constant in size. Only a minimal and functionally non-damaging tissue reaction was observed.

A second hydrogel system using a PVP hydrogel for constant volume formulation was formulated and tested as set forth below.

A solution of 15% PVP K-90 was beamed at 10 Mrad to prepare the PVP material. The gel was dried in a vacuum oven for 3 days. The dried crosslinked PVP was then ground using a Waring grinder to produce a power. The powder was then sifted to the desired range 45–180 microns. Since the PVP swells in glycerin, mineral oil was used as the carrier fluid.

Volume expansion factor for crosslinked PVP=0.07675 gm/cc

True dry density of crosslinked PVP=1.1 gm/cc

Density of mineral oil=0.8737 gm/cc

For a 10 ml constant volume PVP formulation:
0.7675 gm dry crosslinked PVP was mixed with 8.1267 gm of mineral oil creating a 10 ml total volume injection.

EXAMPLE 6
Beagle Dog Urethral Wall Implantation

A constant volume suspension of PVP and mineral oil was injected into a dog's urethra wall using a 20 gauge XXTW hypodermic needle. The dog's urethra was observed using a scope at 3, 7, 10, 14, & 28 days. The boluses appeared to remain constant in size. Only minimal and functionally non-damaging tissue reaction was observed.

EXAMPLE 7
Constant Volume Expansion Tests

The PVP constant volume expansion was tested to insure that the formulation maintains constant volume after the carrier dissipates and the hydrogel particles hydrate. 3 cc of PVP & mineral oil constant volume formulation was washed with isotonic saline to remove the mineral oil and hydrate the PVP. The washed PVP was placed into a 15 cc centrifuge tube. After centrifuging, the hydrate PVP volume was recorded as 3.05 cc.

Another formulation used PVP hydrogel with soybean oil as the carrier. Density of soybean oil is 0.9137 gm/cc. Therefore a 10 cc constant volume suspension consisted of 0.7675 gm dry crosslinked PVP with 8.499 gm soybean oil. A constant volume expansion test, as described above, showed that the formulation maintained constant volume after hydration.

EXAMPLE 8
Biocompatibility in Beagle Dog Urethra Wall

A 28 day study was carried out using PEO in glycerine with the following results:

Gross Observations at Necropsy:
1) No evidence of ulceration or abnormal tissue reaction.
2) Cystoscopy at 10 days showed focal mucosal ulceration; at 28 days this area was a "slit" like mucosal depression, that looked epithelialized at necropsy.

A 28 day study was carried out using PVP in mineral oil with the following results:

Gross Observations at Necropsy:
1) Urinary bladder and urethra within normal limits. Material was implanted periserosal. There was no observed ulceration or extrusion of test material.

2) No material extrusion or ulceration. Urethra was within normal limits.

EXAMPLE 9
Aging of PEO Particles in Glycerine

After 10 months of shelf life, the PEO particles in glycerine remained as distinct particles.

1) PEO particles 63–90 microns suspended in glycerine were placed in a vial on the shelf for 10 months. The particles remained distinct particles in the suspension.
2) PEO particles 125–150 microns suspended in 10% water in glycerine. The suspension was placed into a vial and left on a shelf for 10 months. The particles remained distinct and unswollen particles in the suspension.

Industrial Applicability

Although the physiologically acceptable composition is typically inserted into tissues adjacent to a tissue structure to exert pressure on the selected tissue structure, a specific use for the composition is for increasing urine flow resistance in patients having urinary incontinence. The physiologically acceptable composition is inserted into the tissues surrounding the patient's urethra adjacent to the patient's urethral sphincter. The presence of the physiologically acceptable composition allows constriction of the urethra thereby decreasing urine flow from the bladder. As a result the incontinent patient will have an improved control of urine flow.

The physiologically acceptable composition can also be used in patients having vesicoureteral reflux. Similar to the method used in increasing urine flow resistance in patients having urinary incontinence, the physiologically acceptable composition is injected into the tissues adjacent to the patient's ureteral orifice thereby constricting the ureteral duct. With the constriction, the undesirable backflow of urine from the bladder up the ureter is prevented.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

That which is claimed is:

1. A physiologically acceptable composition comprising a plurality of physiologically acceptable solid polymer particles dispersed in a physiologically acceptable biodissipatable liquid carrier, the composition having a selected volume, the solid polymer particles being a poly(ethylene oxide) (PEO) polymer or copolymer the solid polymer particles being capable of hydrating and on hydration swelling to a predetermined volume and being substantially insoluble in body fluids and being substantially insoluble in and non-swellable by the liquid carrier.

2. A physiologically acceptable composition as set forth in claim 1 wherein the liquid carrier is glycerine.

3. A physiologically acceptable composition as set forth in claim 1 wherein the carrier liquid has a viscosity of no more than about 1,000 cps.

4. A physiologically acceptable composition as set forth in claim 1 wherein the carrier liquid has a viscosity of no more than about 650 cps.

5. A physiologically acceptable composition as set forth in claim 1 wherein the carrier liquid has a viscosity of no more than about 400 cps.

6. A physiologically acceptable composition as set forth in claim 1 wherein the swollen particles have a particle size of at least about 25 microns.

7. A physiologically acceptable composition as set forth in claim 1 wherein the swollen particles have a particle size of at least about 50 microns.

8. A physiologically acceptable composition comprising a plurality of physiologically acceptable solid polymer particles dispersed in a physiologically acceptable biodissipatable liquid carrier, the composition having a selected volume, the solid polymer particles being a poly(ethylene oxide) (PEO) polymer or copolymer or a polyvinylpyrrolidone polymer or copolymer, the solid polymer particles being capable of hydrating and on hydration swelling to a predetermined volume and being substantially insoluble in body fluids and being substantially insoluble in and non-swellable by the liquid carrier wherein the plurality of solid polymer particles is present in a selected concentration such that following insertion into a patient's body it hydrates and swells to the predetermined volume as the liquid carrier dissipates to provide a final volume which is substantially equal to the selected volume.

9. A physiologically acceptable composition as set forth in claim 8 wherein the hydrated solid polymer particles have a particle size sufficient to resist migration from a site of insertion into a patient's body.

10. A physiologically acceptable composition as set forth in claim 9 wherein the hydrophilic component swells up from 30 to 1,000 percent after hydration.

11. A physiologically acceptable composition as set forth in claim 9 wherein the particle size following hydration is at least about 25 microns.

12. A physiologically acceptable composition as set forth in claim 11 wherein the solid polymer particles further comprises a radiopaque material.

13. A physiologically acceptable composition comprising a plurality of physiologically acceptable solid polymer particles dispersed in a physiologically acceptable biodissipatable liquid carrier, the composition having a selected volume, the solid polymer particles being a poly(ethylene oxide) (PEO) polymer or copolymer or a polyvinylpyrrolidone polymer or copolymer, the solid polymer particles being capable of hydrating and on hydration swelling to a predetermined volume and being substantially insoluble in body fluids and being substantially insoluble in and non-swellable by the liquid carrier wherein the solid polymer particles further comprises a radiopaque material.

14. A physiologically acceptable composition comprising a plurality of physiologically acceptable solid polymer particles dispersed in a physiologically acceptable biodissipatable liquid carrier, the composition having a selected volume, the solid polymer particles being a poly(ethylene oxide) (PEO) polymer or copolymer or a polyvinylpyrrolidone polymer or copolymer, the solid polymer particles being capable of hydrating and on hydration swelling to a predetermined volume and being substantially insoluble in body fluids and being substantially insoluble in and non-swellable by the liquid carrier further including a viscosity reducing agent.

15. A physiologically acceptable composition as set forth in claim 14 wherein the viscosity reducing agent is selected from the group consisting of water, isopropyl alcohol, an alcohol of the formula $-CH_3-(CH_2)_x-OH$ where $x<4$, a dialcohol of the formula $HO-(CH_2)_x-OH$ where $x,8$ and an ethylene glycol with molecular weight less than 400.

16. A physiologically acceptable composition comprising a plurality of physiologically acceptable solid polymer particles dispersed in a physiologically acceptable biodissipatable liquid carrier, the composition having a selected volume, the solid polymer particles being a poly(ethylene oxide) (PEO) polymer or copolymer or a polyvinylpyrrolidone polymer or copolymer, the solid polymer particles being capable of hydrating and on hydration swelling to a predetermined volume and being substantially insoluble in body fluids and being substantially insoluble in and non-swellable by the liquid carrier wherein the liquid carrier is mineral oil or a triglyceride oil and the solid polymer particles are a polyvinylpyrrolidone polymer or copolymer.

17. A physiologically acceptable composition as set forth in claim 16, further including a viscosity reducing agent which does not swell the particles when they are dispersed in the liquid carrier.

18. A physiologically acceptable composition comprising a plurality of physiologically acceptable solid polymer particles dispersed in a physiologically acceptable biodissipatable liquid carrier, the composition having a selected volume, the solid polymer particles being a poly(ethylene oxide) (PEO) polymer or copolymer or a polyvinylpyrrolidone polymer or copolymer, the solid polymer particles being capable of hydrating and on hydration swelling to a predetermined volume and being substantially insoluble in body fluids and being substantially insoluble in and non-swellable by the liquid carrier wherein further including a viscosity reducing agent which does not swell the particles when they are dispersed in the liquid carrier.

19. A physiologically acceptable composition as set forth in claim 18 wherein the liquid carrier is selected from the group consisting of glycerine, glycerol monoacetate, glycerol diacetate, polyethylene glycol, diethylene glycol, polyethylene glycol/polypropylene glycol block copolymers, low molecular weight polyethylene oxides, polysorbate and mixtures of the above and the solid polymer particles are glycerine insoluble and non-swellable and the solid polymer particles are a poly(ethylene oxide) (PEO) polymer or copolymer.

20. A method of deforming a selected tissue structure comprising inserting into tissues adjacent the selected tissue structure a physiologically acceptable composition comprising a plurality of physiologically acceptable solid hydrophilic polymer particles dispersed in a physiologically acceptable biodissipatable liquid carrier, the composition having a selected volume, the solid polymer particles being a glycerine insoluble poly(ethylene oxide) (PEO) polymer or copolymer or a mineral oil insoluble polyvinylpyrrolidone polymer or copolymer, the solid polymer particles being capable of hydrating and on hydration absorbing at least 30% water and of swelling to a predetermined volume, the solid polymer particles being substantially insoluble in and non-swellable by the liquid carrier.

21. A method as set forth in claim 20 wherein the plurality of solid polymer particles hydrates and swells to the predetermined volume as the liquid carrier dissipates, the predetermined volume being substantially equal to the selected volume.

22. A method as set forth in claim 20 wherein the carrier liquid has a viscosity of no more than about 1,000 cps and the inserting comprises injecting the composition without use of an injection assist device.

23. A method for increasing urine flow resistance in a patient having urinary incontinence comprising inserting into tissues surrounding the patient's urethra adjacent to the patient's urethral sphincter a selected volume of a physiologically acceptable composition comprising a plurality of physiologically acceptable solid polymer particles dispersed in a physiologically acceptable biodissipatable liquid carrier, the solid polymer particles being a glycerine insoluble poly(ethylene oxide) (PEO) polymer or copolymer or a mineral oil insoluble polyvinylpyrrolidone polymer or copolymer, the solid polymer particles being capable of hydrating and on hydration absorbing at least 30% water and of swelling to a predetermined volume, the solid polymer particles being substantially insoluble in body fluids and being substantially insoluble in and non-swellable by the liquid carrier.

24. A method as set forth in claim 23 wherein the solid polymer particles hydrate and swell to the predetermined volume as the liquid carrier dissipates, the predetermined volume being substantially equal to the selected volume.

25. A method as set forth in claim 23 wherein the carrier liquid has a viscosity of no more than about 1,000 cps and the inserting comprises injecting the composition without use of an injection assist device.

26. A method for treating a patient having vesicoureteral reflux comprising inserting into tissues adjacent the patient's ureteral orifice a selected volume of a physiologically acceptable composition comprising a plurality of physiologically acceptable solid polymer particles dispersed in a physiologically acceptable biodissipatable liquid carrier, the solid polymer particles being a glycerine insoluble poly(ethylene oxide) (PEO) polymer or copolymer or a mineral oil insoluble polyvinylpyrrolidone polymer or copolymer, the solid polymer particles being capable of hydrating and on hydration absorbing at least 30% water and of swelling to a predetermined volume, the solid particles being substantially insoluble in body fluids and being substantially insoluble in and non-swellable by the liquid carrier.

27. A method as set forth in claim 26 wherein the solid polymer particles hydrates and swells to the predetermined volume as the liquid carrier dissipates, the predetermined volume being substantially equal to the selected volume.

28. A method as set forth in claim 26 wherein the carrier liquid has a viscosity of no more than about 1,000 cps and the inserting comprises injecting the composition without use of an injection assist device.

29. A method as set forth in claim 28 wherein the carrier liquid has a viscosity of no more than about 1,000 cps and the inserting comprises injecting the composition without use of an injection assist device.

30. A method of deforming a selected tissue structure comprising inserting into tissues adjacent the selected tissue structure a selected volume of a physiologically acceptable composition comprising a plurality of physiologically acceptable solid polymer particles dispersed in a physiologically acceptable biodissipatable liquid carrier, the solid polymer particles being a glycerine insoluble poly(ethylene oxide) (PEO) polymer or copolymer or a mineral oil insoluble polyvinylpyrrolidone polymer or copolymer, the plurality of solid polymer particles being capable of hydrating and upon hydration absorbing at least about 30% water and of swelling to a predetermined volume, the solid particles being substantially insoluble in body fluids and being substantially insoluble in and non-swellable by the liquid carrier.

31. A method as set forth in claim 30 wherein the plurality of solid polymer particles swells to the predetermined volume as the liquid carrier dissipates, the predetermined volume being substantially equal to the selected volume.

32. A method for increasing urine flow resistance in a patient having urinary incontinence comprising inserting into tissues surrounding the patient's urethra adjacent to the patient's urethral sphincter a selected volume of a physiologically acceptable composition comprising a plurality of physiologically acceptable solid hydrophilic polymer particles dispersed in a physiologically acceptable biodissipatable liquid carrier, the solid polymer particles being a glycerine insoluble poly(ethylene oxide) (PEO) polymer or copolymer or a mineral oil insoluble polyvinylpyrrolidone polymer or copolymer, the plurality of solid polymer particles being capable of hydrating and upon hydration absorbing at least about 30% water and of swelling to a predetermined volume, the solid particles being substantially insoluble in body fluids and being substantially insoluble in and non-swellable by the liquid carrier.

33. A method as set forth in claim 32 wherein the solid polymer particles swells to the predetermined volume as the liquid carrier dissipates, the predetermined volume being substantially equal to the selected volume.

34. A method as set forth in claim 32 wherein the carrier liquid has a viscosity of no more than about 1,000 cps and the inserting comprises injecting the composition without use of an injection assist device.

35. A method for treating a patient having vesicoureteral reflux comprising inserting into tissues adjacent the patient's ureteral orifice a selected volume of a physiologically acceptable composition comprising a plurality of physiologically acceptable solid polymer particles in a physiologically acceptable biodissipatable liquid carrier, the solid polymer particles being a glycerine insoluble poly(ethylene oxide) (PEO) polymer or copolymer or a mineral oil insoluble polyvinylpyrrolidone polymer or copolymer, the plurality of solid polymer particles being capable of hydrating and upon hydration absorbing at least about 30% water and of swelling to a predetermined volume, the solid particles being substantially insoluble in body fluids and being substantially insoluble in and non-swellable by the liquid carrier.

36. A method as set forth in claim 35 wherein the solid polymer particles hydrates and swells to the predetermined volume as the liquid carrier dissipates, the predetermined volume being substantially equal to the selected volume.

37. A method as set forth in claim 35 wherein the carrier liquid has a viscosity of no more than about 1,000 cps and the inserting comprises injecting the composition without use of an injection assist device.

* * * * *